US00PP37247P2

(12) United States Plant Patent
van der Eijk

(10) Patent No.: US PP37,247 P2
(45) Date of Patent: Feb. 3, 2026

(54) ***PHILODENDRON* PLANT NAMED 'WHIWAMIN'**

(50) Latin Name: ***Philodendron* sp.**
Varietal Denomination: WHIWAMIN

(71) Applicant: VDE Plant B.V., Woubrugge (NL)

(72) Inventor: Edwin van der Eijk, Woubrugge (NL)

(73) Assignee: VDE Plant B.V., Woubrugge (NL)

( * ) Notice: Subject to any disclaimer, the term of this patent is extended or adjusted under 35 U.S.C. 154(b) by 0 days.

(21) Appl. No.: 18/831,410

(22) Filed: Jan. 21, 2025

(51) Int. Cl.
*A01H 5/12* (2018.01)
*A01H 6/10* (2018.01)

(52) U.S. Cl.
USPC ..... Plt./381
CPC ..... *A01H 6/10* (2018.05); *A01H 5/12* (2013.01)

(58) Field of Classification Search
USPC ..... Plt./381
CPC ..... A01H 5/12; A01H 5/00; A01H 6/10
See application file for complete search history.

(56) References Cited

U.S. PATENT DOCUMENTS

2024/0172572 P1 * 5/2024 Gregory ..... Plt./381

* cited by examiner

*Primary Examiner* — June Hwu
(74) *Attorney, Agent, or Firm* — Samuel R. McCoy, Jr.

(57) ABSTRACT

'WHIWAMIN' is a distinctive *Philodendron* plant which is characterized by the combination of a small stature, a compact growth habit with an abundance of uniquely variegated foliage, white juvenile foliage that is suffused and mottled with green in between the lateral veins, dark green mature foliage with white suffusion immediately adjacent to the lateral veins, and the uniformity and stability of these characteristics from generation to generation.

3 Drawing Sheets

Latin name of the genus and species: The Latin name of the genus and species of the novel variety disclosed herein is *Philodendron* sp.

Variety denomination: The inventive variety of *Philodendron* disclosed herein has been given the variety denomination 'WHIWAMIN'.

BACKGROUND OF THE INVENTION

Parentage: 'WHIWAMIN' originated as a spontaneous whole-plant mutation of *Philodendron* sp. 'White Wave' (not patented), and was first observed by the inventor in March of 2021 at a commercial greenhouse in Woubrugge, Netherlands. Between the years 2019 and 2021, the inventor discovered a plurality of whole-plant mutations growing amongst a series of cultivated populations of 'White Wave' plants which were themselves produced using meristematic tissue culture micropropagation. Each mutation exhibited unique foliage coloration and variegation patterns relative to the parent and all other progeny. The mutations were asexually propagated by harvesting shoots from the mother plant. The resulting accessions produced from each mutation were then grown to maturity to assess the stability of the traits first observed and to further evaluate for other traits which may prove desirable for commercial production and sales, namely compactness and improved plant vigor. In July of 2021, it was determined that one of the mutations, originally discovered in March of 2021, exhibited the combination of unique, stable variegation, compactness, a relative abundance of foliage, and vigorous growth. The new plant was given the name, 'WHIWAMIN'.

Asexual Reproduction: 'WHIWAMIN' was first asexually reproduced in July of 2021 in Woubrugge, Netherlands by dividing the basal shoots of the mother plant. The claimed plant was later asexually reproduced by way of meristematic tissue culture. Through four subsequent generations, the unique features of this cultivar have proven to be stable and true to type.

SUMMARY OF THE INVENTION

The cultivar 'WHIWAMIN' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'WHIWAMIN'. These characteristics in combination distinguish 'WHIWAMIN' as a new and distinct *Philodendron* cultivar:

1. *Philodendron* 'WHIWAMIN' exhibits a compact growth habit with an abundance of small, variegated laminas borne on short petioles; and
2. *Philodendron* 'WHIWAMIN' exhibits white juvenile foliage that is suffused and mottled with green in between the lateral veins; and
3. *Philodendron* 'WHIWAMIN' exhibits dark green mature foliage with white suffusion immediately adjacent to the lateral veins.

BOTANICAL DESCRIPTION OF THE PLANT

Figure 1:
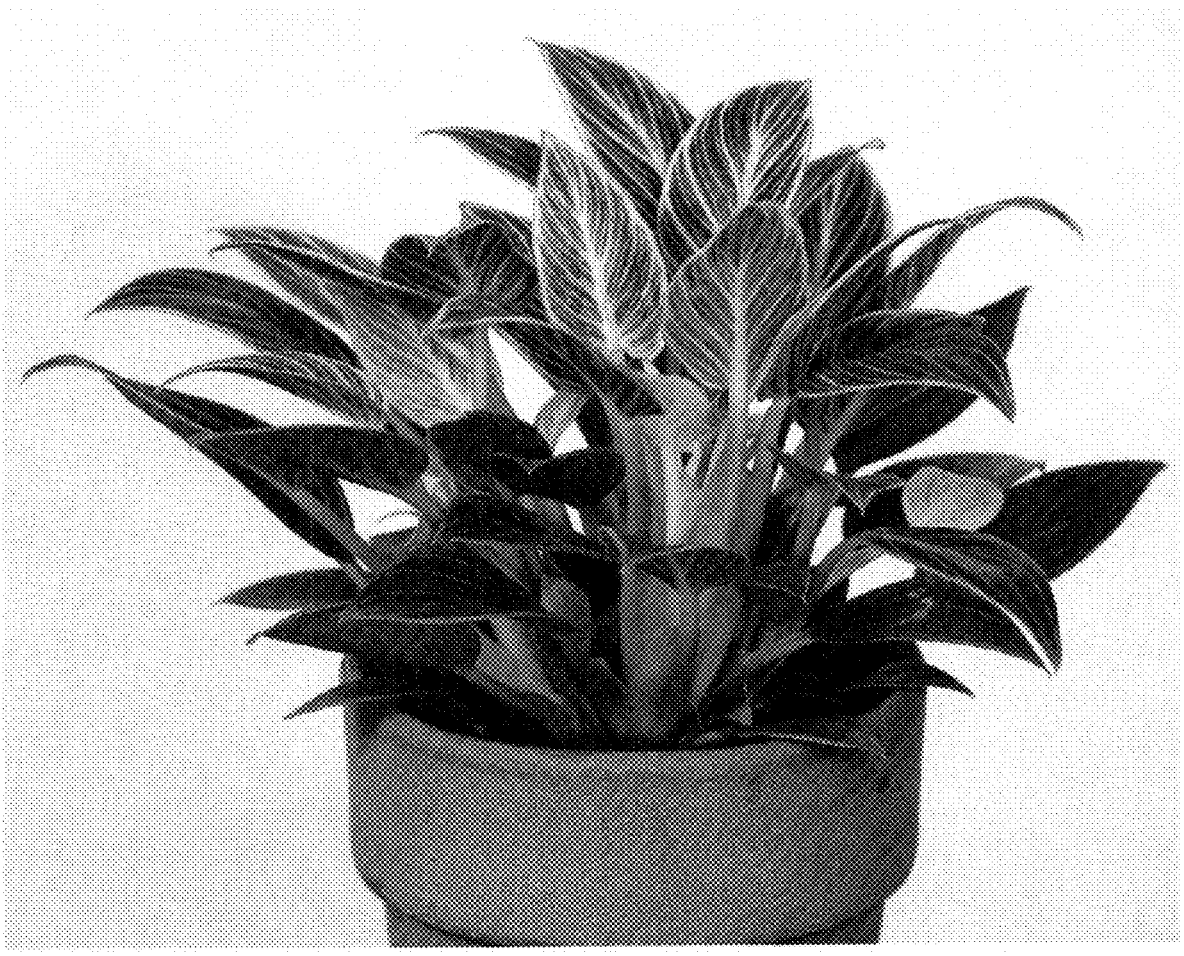
FIG. 1 illustrates, as nearly true as it is reasonably possible to make the same in color photographs of this type, an exemplary plant of 'WHIWAMIN' grown in a climate-controlled greenhouse in Woubrugge, Netherlands. This plant is approximately 6 months old, in a 12 cm container.
Figure 2:
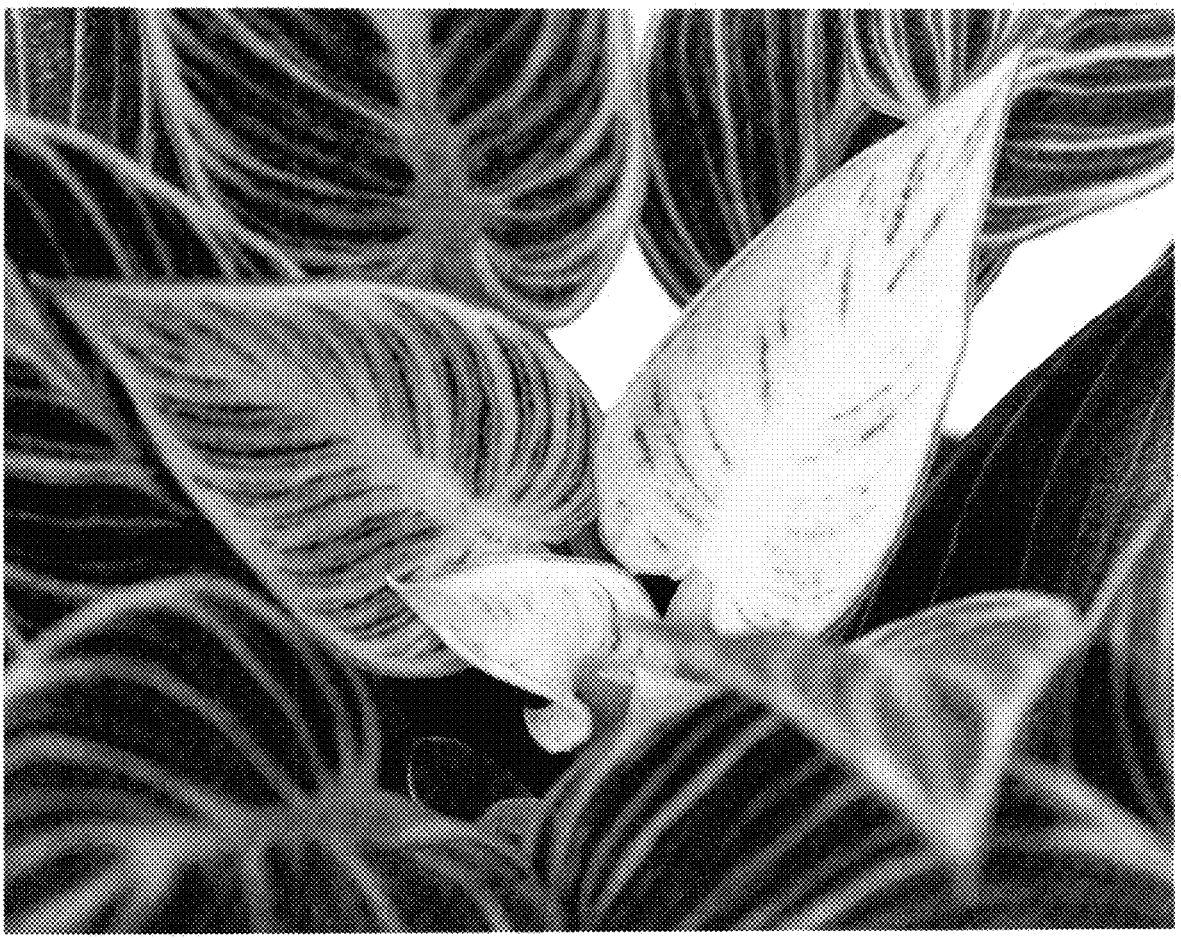
FIG. 2 illustrates, as nearly true as it is reasonably possible to make the same in color photographs of this type, the adaxial surface of the juvenile foliage of 'WHIWAMIN'.
Figure 3:
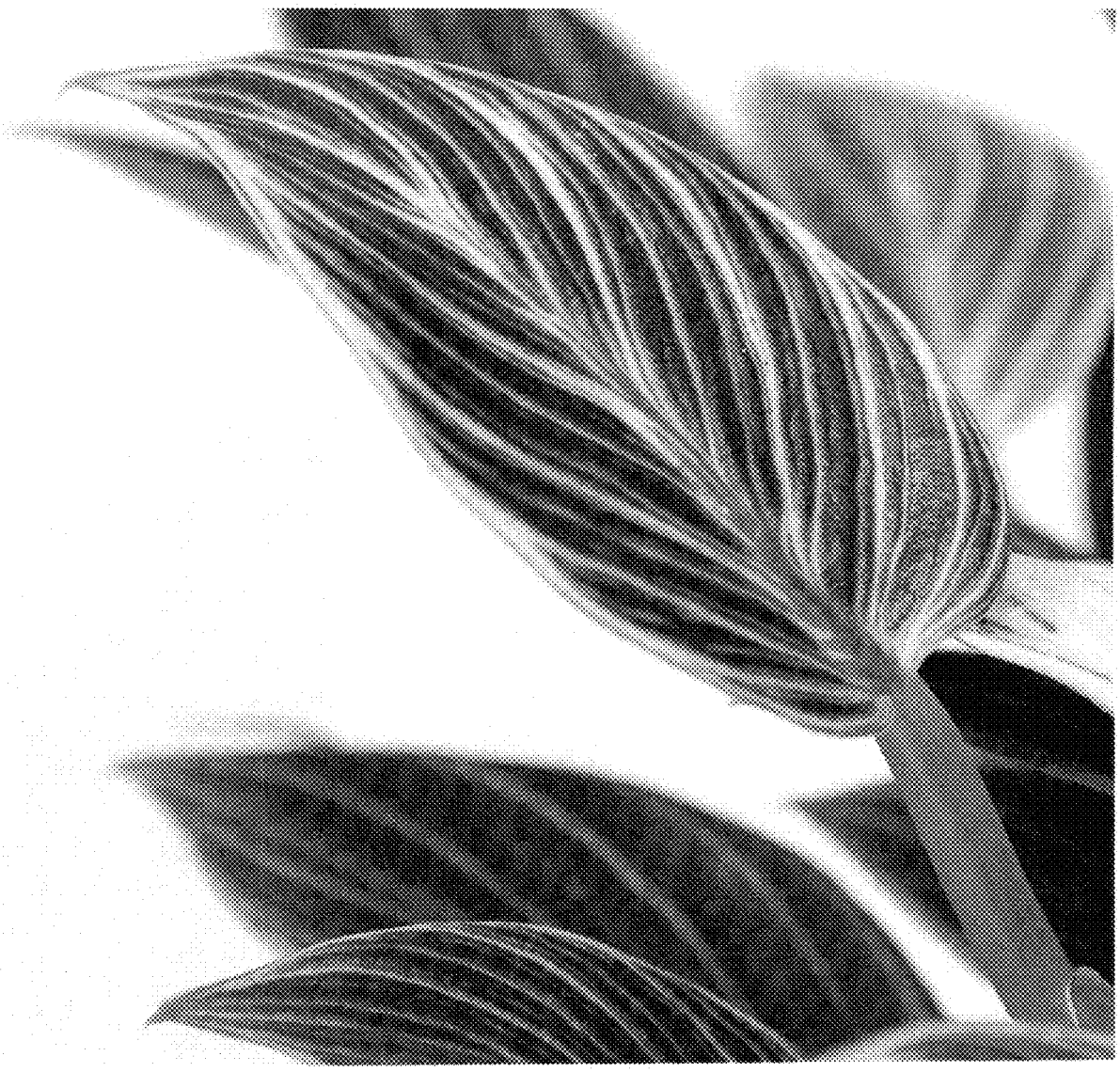
FIG. 3 illustrates, as nearly true as it is reasonably possible to make the same in color photographs of this type, the adaxial surface of the mature foliage of 'WHIWAMIN'.

The following observations and measurements, made in November of 2023, describe averages from a 12-month-old 'WHIWAMIN' plant grown in 12 cm nursery containers at a climate-controlled greenhouse in Woubrugge, Netherlands. The plants were grown under shade cloth, with regular drip irrigation. During production, no supplemental fertilizer applications or chemical pest treatments were made to the plants and no photoperiodic treatments were utilized in production.

Those skilled in the art will appreciate that certain characteristics will vary with older or, conversely, with younger plants. 'WHIWAMIN' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, Sixth Edition.

A botanical description of 'WHIWAMIN' and a comparison with the parent plant and most similar commercial cultivar are provided below.

Plant description:

*Growth habit*.—Broad spreading to upright herbaceous perennial with foliage growth from basal shoots.

*Plant profile shape*.—Flattened globular.

*Height from soil level to top of foliar plane*.—16.0 cm.

*Plant spread*.—27.5 cm.

*Number of basal shoots per plant*.—6.

*Propagation*.—Type — Asexual propagation is accomplished by way of stem and leaf cuttings which root well without rooting compound or hormone. Time to initiate rooting — Approximately 10 to 21 days at 22 degrees Celsius. Time to produce a rooted cutting — Approximately 6 to 9 months, at an ambient temperature range of 22 degrees Celsius, are needed to produce a marketable finished plant from a rooted cutting.

*Disease and pest resistance or susceptibility*.—Neither susceptibility nor resistance to pests and diseases common to either *Philodendron* have been observed.

*Environmental tolerances*.—Adapt to temperatures as low as 5 degrees Celsius and at least as high as 40 degrees Celsius; moderate to high tolerance to rain; low to moderate tolerance to wind.

Roots:

*Density*.—Not very dense.

*Length*.—12.4 cm.

*Diameter*.—0.25 cm.

*Texture*.—Fleshy, non-fibrous.

*Color*.—Greyed-orange, RHS 164B.

Foliage:

*Phyllotaxy*.—Leaves emerge directly from the plant base in an alternate arrangement.

*Attachment*.—Petiolate.

*Division*.—Simple.

*Attitude*.—Juvenile foliage is nearly vertical and becomes more relaxed as the foliage matures.

*Quantity*.13 12 leaves per shoot.

*Lamina*.—Shape — Ovate. Length — 7.2 cm, excluding the petiole. Width — 3.4 cm. Apex — Apiculate. Base — Rounded to truncate. Aspect — Flat to slightly carinate and curled downward; margins are narrowly revolute. Margins — Entire, with no undulation. Texture and luster, adaxial surface — Smooth, glabrous and moderately glossy. Texture and luster, abaxial surface — Smooth, glabrous and slightly glossy. Color — Juvenile foliage, adaxial surface — White, RHS 155C; areas in between lateral veins are suffused or otherwise mottled with green, nearest to a combination of RHS 141A, 141B, 141C, and 141D. Juvenile foliage, abaxial surface — White, RHS 155C; areas in between lateral veins are suffused or otherwise mottled with green, nearest to a combination of RHS 141B, 141C, and 141D. Mature foliage, adaxial surface — Nearest to a mixture of yellow-green and greyed-green, RHS 147A and N189A yet slightly darker. The areas immediately adjacent to the lateral veins is moderately to heavily suffused with white, RHS 155C. Mature foliage, abaxial surface — Green, nearest to RHS 138A. The areas immediately adjacent to the lateral veins is moderately to heavily suffused with white, RHS 155C. Venation — Pattern — Pinnate. Color, adaxial surface of juvenile foliage — White, nearest to RHS 155C. Color, abaxial surface of juvenile foliage — White, nearest to RHS 155C. Color, adaxial surface of mature foliage — The main vein is yellow-green, nearest to in between RHS 145B and 145C, and irregularly flecked and striated with white, nearest to RHS 155C. The lateral veins are yellow-green, in between RHS 145B and 145C. Color, abaxial surface of mature foliage — The main vein is yellow-green, nearest to RHS 145D, and irregularly flecked and striated with white, nearest to RHS 155C. The lateral veins are yellow-green, RHS 145D.

*Petiole*.—Aspect — Ovoid. Strength — Moderately strong. Aspect — Subterete. Length — 8.0 cm. Width — 0.4 cm. Texture and luster, adaxial surface — Smooth, glabrous and slightly glossy. Texture and luster, abaxial surface — Smooth, glabrous and moderately glossy. Juvenile color, adaxial surface — Yellow-green, nearest to RHS 147B, and longitudinally striped with green, RHS 143B; petiole coloration transitions to white distally, at and near the point of attachment with the lamina, nearest to RHS 155C. Juvenile color, abaxial surface — Yellow-green, nearest to RHS 147A, and longitudinally striped with green, RHS 143B; petiole coloration transitions to white distally, at and near the point of attachment with the lamina, nearest to RHS 155C. Mature color, adaxial surface — Yellow-green, nearest to a mixture of RHS 144A and 144B, and longitudinally striped with green, RHS 143B. Mature color, abaxial surface — Yellow-green, nearest to a mixture of RHS 144B and 144C, and longitudinally striped with green, RHS 143B. Petiole Wings — Position — Proximal end of the petiole. Length — 5.8 cm. Width — 0.5 cm. Color, adaxial surface — Yellow-green, nearest to RHS 144B. Color, abaxial surface — Yellow-green, nearest to RHS 144B, and longitudinally striped with green, nearest to RHS 143B.

Inflorescence: To date, 'WHIWAMIN' has not flowered.

COMPARISONS WITH THE PARENT PLANT AND CLOSEST KNOWN COMMERCIAL COMPARATOR

Plants of the new cultivar 'WHIWAMIN' differ from the seed parent, *Philodendron* 'White Wave' (not patented), by the characteristics described in Table 1 below.

TABLE 1

| Characteristic | 'WHIWAMIN' | 'White Wave' |
|---|---|---|
| Growth habit. | More compact than 'White Wave'. | Less compact than 'WHIWAMIN'. |
| Plant size. | Smaller than 'White Wave'. | Larger than 'WHIWAMIN'. |
| Foliage size. | Significantly smaller laminas and shorter petioles relative to 'White Wave'. | Larger laminas and longer petioles relative to 'WHIWAMIN'. |

COMPARISONS WITH THE CLOSEST KNOWN COMPARATOR

Plants of the new cultivar 'WHIWAMIN' differ from the closest known commercial comparator, *Philodendron* hybrid 'Rojo Congo' (U.S. Plant Pat. No. 14,116), in the following characteristics described in Table 2 below.

TABLE 2

| Characteristic | 'WHIWAMIN' | 'Rojo Congo' |
|---|---|---|
| Growth habit. | More compact than 'Rojo Congo'. | Less compact than 'WHIWAMIN'. |
| Foliage size. | Smaller laminas and shorter petioles relative to 'Rojo Congo'. | Larger laminas and longer petioles relative to 'WHIWAMIN'. |
| General coloration of the juvenile petiole. | Yellow-green, longitudinally striped with green, and transitioning to white at and near the point of attachment to the lamina. | Yellow-green. |
| General coloration of the juvenile foliage. | White, with green suffusion and mottling in the areas between the lateral veins. | Maroon. |
| General coloration of the of the mature foliage. | Dark green with white suffusion immediately adjacent to the lateral veins. | Yellow-green and heavily suffused with a mixture of copper and burgundy. |

That which is claimed is:

1. A new and distinct variety of *Philodendron* plant named 'WHIWAMIN', substantially as described and illustrated herein.

* * * * *